US00PP14974P3

(12) United States Plant Patent
McCrory

(10) Patent No.: US PP14,974 P2
(45) Date of Patent: Jun. 29, 2004

(54) GUZMANIA PLANT NAMED 'GEORGIA'

(50) Latin Name: *Guzmania lingulata×Guzmania wittmackii*
Varietal Denomination: Georgia

(75) Inventor: Ward McCrory, Eustis, FL (US)

(73) Assignees: Corn.Bak B.V., Assendelft (NL); McCrory's Sunny Hill Nursery Inc., Eustis, FL (US)

( * ) Notice: Subject to any disclaimer, the term of this patent is extended or adjusted under 35 U.S.C. 154(b) by 48 days.

(21) Appl. No.: 10/230,237

(22) Filed: Aug. 29, 2002

(65) Prior Publication Data

US 2004/0045068 P1 Mar. 4, 2004

(51) Int. Cl.[7] ..... A01H 5/00

(52) U.S. Cl. ..... Plt./371

(58) Field of Search ..... Plt./371

*Primary Examiner*—Kent Bell

(74) *Attorney, Agent, or Firm*—Foley & Lardner LLP

(57) ABSTRACT

A new and distinct Guzmania plant named 'Georgia' characterized by being a solid, tenable, long-lasting hybrid; having superior bract production; compound red inflorescence RHS 44 A; and variegated leaves, green RHS 137 A on the sides and light greyed-yellow RHS 160 C in the center.

3 Drawing Sheets

Latin name of the genus and species of the plant claimed: Mutation of *Guzmania lingulata×Guzmania wittmackii.*
Variety denomination: Georgia.

BACKGROUND OF THE INVENTION

The present invention relates to a new, distinct and stable plant of Guzmania hereinafter referred to as 'Georgia'. Guzmania is a member of the Bromeliaceae family.

Guzmania comprise a genus of over 100 species of evergreen perennials suitable for cultivation in the home under glass. Guzmania are predominantly epiphytic with a few terrestrial species and are native to the tropics. For the most part the species vary in diameter from 7 or 8 inches to 3 or 4 feet and have rosettes of glossy, smooth edged leaves.

Floral bracts of Guzmania frequently have brilliant colors and may last for many months. The range of colors for Guzmania is generally from yellow through orange but may also include flame red and red-purple. White or yellow, tubular, three petalled flowers may also appear on a stem or within the leaf rosette but are usually short lived.

Guzmania may be advantageously grown as pot plants for greenhouse or home use. Desirably the plants are shaded from direct sunlight and during the spring to autumn period, the central vase-like part of the leaf rosette is desirably filled with water.

Guzmania is native to tropical America. Leaves of the Guzmania are usually formed as basal rosettes which are stiff and entire and in several vertical ranks. Guzmania have terminal spikes or panicles which are often bracted with petals united in a tube about as long as the calyx. The ovary is superior and the seeds plumose.

Asexual propagation of Guzmania is frequently done through the use of tissue culture practices. Propagation can also be from off-shoots produced by the plant which may then be rooted. The resulting plantlets are detached from the mother plant and may be potted up in a suitable growing mixture.

The present invention was created by the inventor, Ward McCory in 1993, and flowered for the first time in 1994 in Eustis, Fla. The new cultivar was developed through a controlled breeding program and exhibits unique, desirable and stable characteristics.

The new hybrid Guzmania 'Georgia' is a naturally occurring branch mutation of *Guzmania lingulata×Guzmania wittmackii* 'Rana' (U.S. Plant Pat. No. 7,471). Assexual reproduction of this new cultivar by offshoots in Eustis, Fla., has demonstrated that the combination of characteristics as herein disclosed for the new cultivar are firmly fixed and retained through successive generations of asexual reproduction. The new cultivar reproduces true-to-type.

BRIEF SUMMARY OF THE INVENTION

The following traits have been repeatedly observed and are determined to be basic characteristics of 'Georgia' which in combination distinguish this Guzmania as a new and distinct cultivar:

1. Solid, tenable, long-lasting hybrid;
2. superior bract production;
3. compound red inflorescence RHS 44 A; and
4. variegated leaves, green RHS 137 A on the sides and light greyed-yellow RHS 160 C in the center.

'Georgia' has not been observed under all possible environmental conditions. The phenotype of the new cultivar may vary significantly with variations in environment such as temperature, light intensity, and daylength without any change in the genotype of the plant. The following observations, measurements, and values describe the new cultivar as grown in Assendelft, The Netherlands under conditions which closely approximate those generally used in commercial practice.

Of the many commercial cultivars known to the present inventor, the closest comparison cultivar is Guzmania 'Rana'. The most important difference between 'Georgia' and 'Rana' is the color of the leaves: 'Georgia' has variegated leaves, green on the sides and greyed-yellow in the middle, while 'Rana' does not have variegated leaves.

BRIEF DESCRIPTION OF THE DRAWINGS

The first drawing shows the cultivar 'Georgia'.

The photograph shows a whole plant view of the inflorescence and foliage.

The second drawing shows a close up view of the inflorescence of 'Georgia'.

The third drawing shows a close-up view of the foliage pattern and coloration.

DETAILED BOTANICAL DESCRIPTION

The following observations, measurements and values describe the new cultivar as grown in Eustis, Fla. under conditions which closely approximate those generally used in commercial practice.

In the following description, color references are made to The Royal Horticultural Society Colour Chart (R.H.S.), except where general colors of ordinary significance are used. The age of the plants described is approximately 14 months from potting, as grown in 6 inch containers.

Plant:

*Form.*—Funnel form rosette.

*Height.*—Approximately 65 cm high (flowering).

*Diameter.*—Approximately 75 cm.

*Growth habit.*—Typical to bromeliads, the plant grows without a stem with the leaves forming a cup to hold rainwater.

*Vigor.*—The new cultivar flowers approximately 16 weeks after treatment with Acetylene.

Foliage:

*Size.*—Approximately 40 cm in length.

*Shape.*—Linear lanceolate, entire margin.

*Surface texture.*—Smooth.

*Upper side color.*—Variegated, sides are green, RHS 137 A; center is light greyed-yellow RHS 160 C with one or more green stripes, RHS 137 A.

*Underside color.*—Variegated, green RHS 137 B; center light yellow RHS 16 D (color dependent on environmental conditions).

*Apex.*—Acute.

Flowers:

*Borne.*—Erect stalks.

*Inflorescence type.*—Compound.

*Shape of inflorescence.*—Densely bipinnate.

*Size of the inflorescence.*—Approximately 18 cm in length (on the stalk); approximately 22 cm in diameter.

*Number of flowers per inflorescence.*—Approximately 80.

*Lastingness of the inflorescence.*—A fully grown plant can produce an inflorescence containing approximately 80 flowers and can bloom anytime throughout the year starting approximately 16 weeks after natural induction or induction with acetylene. Each flower blooms for one day and the total length of blooming of the whole inflorescence is 6 weeks.

*Individual petals.*—3 petals per flower, linear in shape with obtuse apex; approximately 5 cm in length; 0.5 cm in width, creamy-white in color, RHS 155D, (disposed within the inflorescence).

*Sepals.*—3 sepals per flower, linear in shape with acute apex and entire margin; transparent to white-ish in color.

*Buds.*—0.4 in diameter; grows to 3 cm in length just before flowering, obtuse apex; white in color, RHS, 155D.

Bracts:

*Scape bract.*—Approximately 30 cm (lowest) to approximately 15 cm just below the primary bracts in length; approximate 3.5–4.5 cm in width; approximately 10 in number; lanceolate shape; smooth texture; margin entire; acute apex; lower scape bracts are the same color as the leaves with a little red RHS 44A at the base; the higher scape bracts are red RHS 44A (upper, inner surface) and red RSH 44C (underside, outside surface).

*Primary bract.*—Approximately 15 cm (lowest) to approximately 8 cm at the top in length; approximately 1–3.5 cm in width; approximately 13 in number; lanceolate shape; smooth texture; margin entire; acute apex; general color RHS 44 A (both surfaces), no variegation, apex of the lowest primary bracts are green RHS 137A at the sides and light greyed-yellow in the center RHS 160C; the higher primary bracts are red to the apex with a yellow-ish base RHS 160A (outer surface), RHS 160C (inner surface) with green at the sides RHS 144A (outer surface) and RHS 144C (inner surface).

*Floral bract.*—Approximately 5 cm long to approximately 2 cm wide; one floral bract per flower; linear-lanceolate shape; obtuse apex; transparent to white-ish in color with some reddish RHS 44A at the surface.

Seeds/fruit: None, sterile.

Reproductive organs:

*Ovaries.*—Superior.

*Stamens.*—6.

*Pollen.*—None produced.

Disease/pest resistance/susceptibility: No information to date.

I claim:

1. A new and distinct Guzmania plant named 'Georgia', substantially as illustrated and described herein.

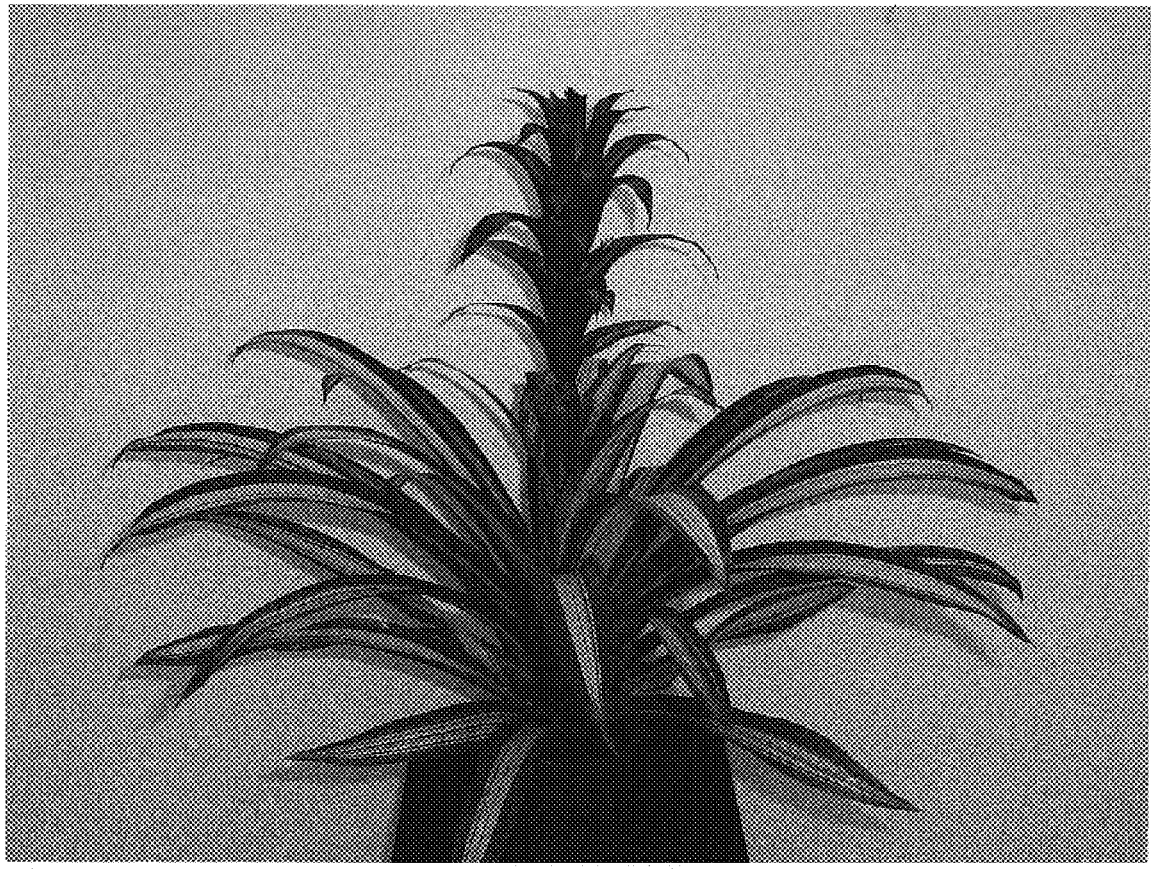

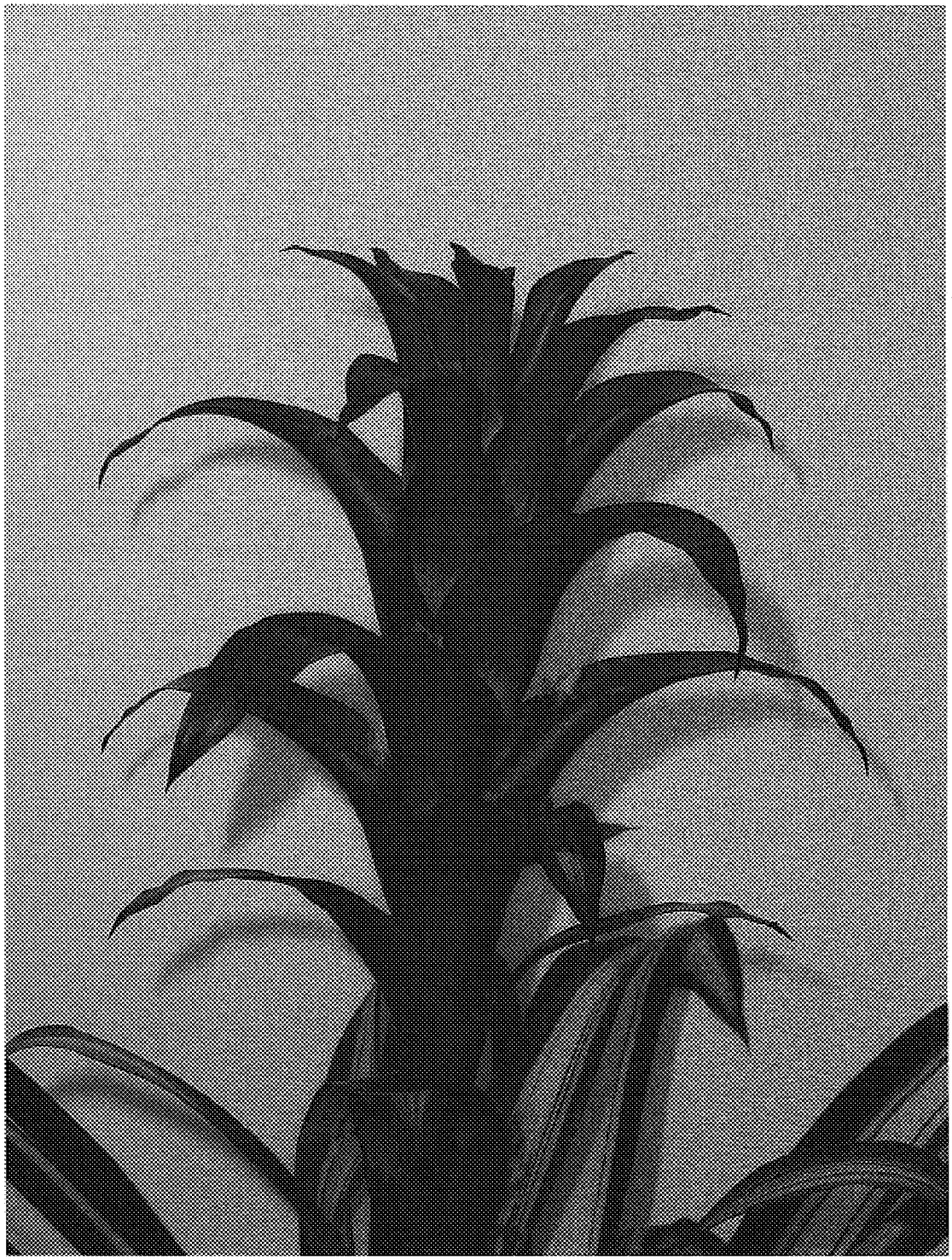

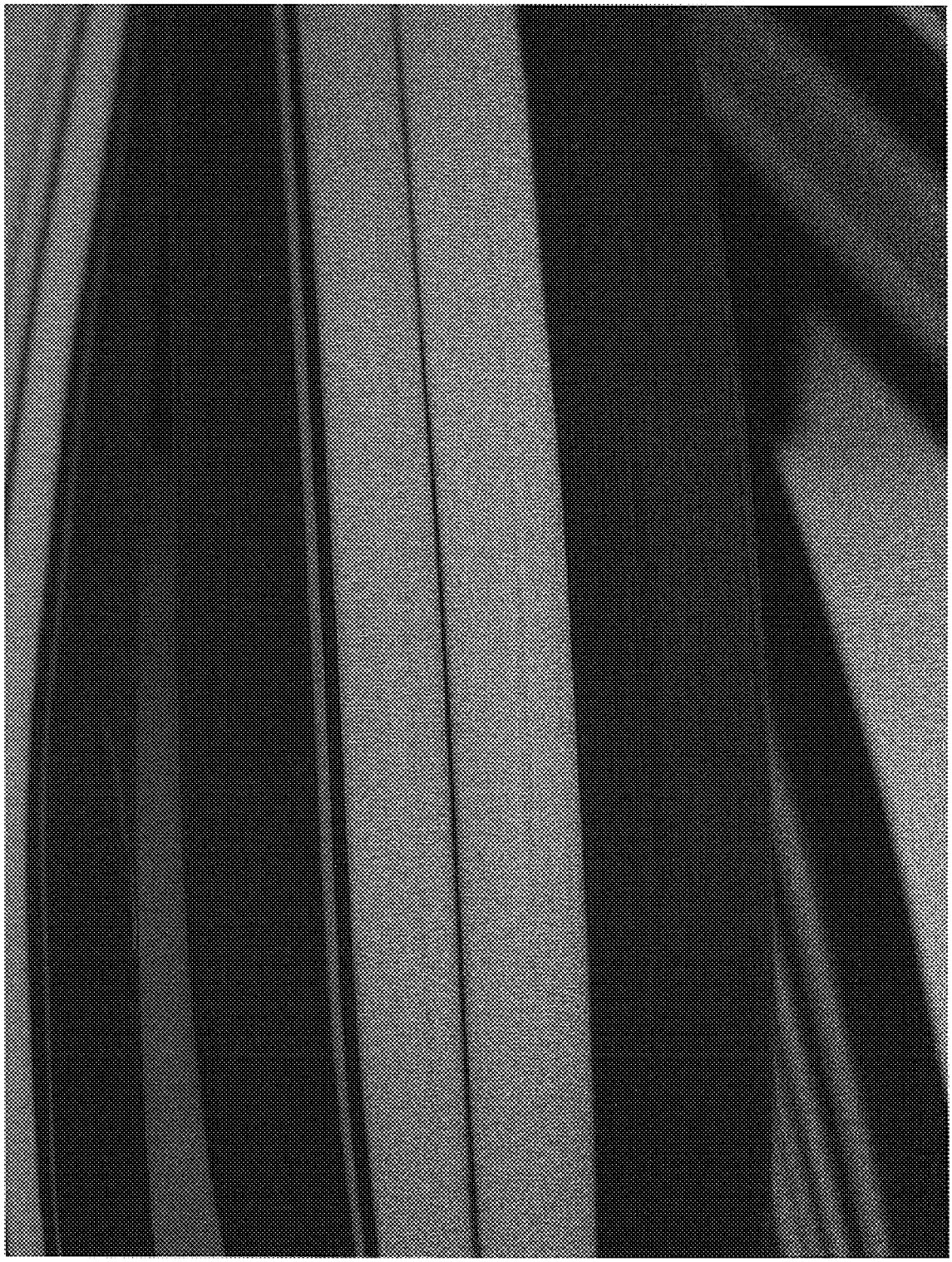

* * * * *